(12) United States Patent
Nishio et al.

(10) Patent No.: US 8,197,651 B2
(45) Date of Patent: Jun. 12, 2012

(54) ION-SELECTIVE ELECTRODE

(75) Inventors: Yuji Nishio, Kyoto (JP); Yasukazu Iwamoto, Kyoto (JP)

(73) Assignee: Horiba, Ltd., Kyoto (JP)

( * ) Notice: Subject to any disclaimer, the term of this patent is extended or adjusted under 35 U.S.C. 154(b) by 81 days.

(21) Appl. No.: 12/744,649

(22) PCT Filed: Dec. 17, 2008

(86) PCT No.: PCT/JP2008/072914
§ 371 (c)(1),
(2), (4) Date: May 25, 2010

(87) PCT Pub. No.: WO2009/078418
PCT Pub. Date: Jun. 25, 2009

(65) Prior Publication Data
US 2010/0252431 A1     Oct. 7, 2010

(30) Foreign Application Priority Data

Dec. 18, 2007 (JP) .................... P2007-325375

(51) Int. Cl.
*G01N 27/333* (2006.01)
(52) U.S. Cl. .................... 204/420; 204/433
(58) Field of Classification Search ............ 204/420, 204/416, 419, 433, 435; 501/46–79; 324/438
See application file for complete search history.

(56) References Cited

U.S. PATENT DOCUMENTS

| 4,957,883 A * | 9/1990 | Kobayashi et al. ............ 501/35 |
| 5,431,800 A * | 7/1995 | Kirchhoff et al. ........ 204/403.01 |
| 2005/0082167 A1* | 4/2005 | Iwamoto et al. ............ 204/433 |

FOREIGN PATENT DOCUMENTS

| JP | 56-130648 | 10/1981 |
| JP | 63-037254 | 2/1988 |
| JP | 02-293343 | 12/1990 |
| JP | 11-295262 | 10/1999 |
| JP | 2003-201145 | 7/2003 |
| JP | 2006-032129 | 2/2006 |

OTHER PUBLICATIONS

Das, Oxynitride glasses—An Overview, Bull. Mater. Sci., vol. 23, 6, 2000, 499-507.*
Fischer et al., The crystal lattice thermal expansion of an oxynitride glass-ceramice material of high-quartz structure, Journal of Materials Science, 20, 1985, 4117-4122.*
Hisato Yoshimura et al. "Theory and Determination of pH, New Edition", Maruzen Co., Ltd., pp. 207-211, with partial English translation.

* cited by examiner

*Primary Examiner* — Alex Noguerola
*Assistant Examiner* — Gurpreet Kaur

(57) ABSTRACT

Disclosed is an ion-selective electrode having excellent mechanical strength, excellent durability, low membrane resistance and good ion response accuracy. This ion-selective electrode comprises a response glass membrane which has ion selectivity and is made of an oxynitride glass containing Li.

12 Claims, 2 Drawing Sheets

ION-SELECTIVE ELECTRODE

TECHNICAL FIELD

The present invention relates to an ion-selective electrode excellent in mechanical strength and durability, low in membrane resistance, and high in ion response accuracy.

BACKGROUND ART

Conventionally, silicate glass is used for a response glass membrane of an ion-selective electrode. Such glass is required to have such properties as small alkali error, small acid error, good response, high chemical durability, an experimental value of a potential gradient close to a theoretical value, low electrical resistance, high mechanical strength, and easiness to machine.

To improve these properties, attempts have been made to add modified metal of various types to the silicate glass. To improve the durability of the silicate glass, in particular, an attempt has been made to add an element of a cation species to the silicate glass. By way of example, it is known that a small amount of La that is a trivalent element is contained in the silicate glass so as to improve the chemical durability (including water resistance) of the silicate glass (Non-Patent Document 1).

La is filled up in a mesh structure of the glass, tightens meshes, generates a hydrated gel layer having a constant thickness, and contributes to improving the water resistance of the glass. In addition, La is a trivalent element and an ion radius of La is relatively large. As a result, an electrostatic force of a univalent anion formed by four-oxygen coordination is low. That is why La makes it difficult to respond to alkali metal, or makes it difficult to cause alkali error. For similar reasons, there is known an example of adding a lanthanoid element other than La to the silicate glass in place of La.

There is also known an attempt to add another rare-earth metal (La, Y, Nd, Ce or the like) to the silicate glass (Patent Document 1).

Non-Patent Document 1: Hisato Yoshimura et al., *New Edition, Theory and Determination of pH*, Maruzen Co., Ltd.

Patent Document 1: Japanese Unexamined Patent Publication No. 1990-293343

Patent Document 2: Japanese Unexamined Patent Publication No. 2006-32129

DISCLOSURE OF THE INVENTION

Problems to be Solved by the Invention

On the other hand, there is no report of any attempt to substitute oxygen atom contained in the silicate glass used for the response glass membrane corresponding to various ions with an element of an anion species.

The Patent Document 2 discloses phosphate-based oxynitride glass in which oxygen contained in phosphate glass is substituted with nitride that is an anion species and which has lithium ion conductivity. However, the phosphate-based oxynitride glass does not have ion selectivity, is low in mechanical strength, and is inferior in durability.

It is, therefore, an object of the present invention to provide an ion-selective electrode excellent in mechanical strength and durability, low in membrane resistance, and high in ion response accuracy.

Means to Solve the Problems

That is, an ion-selective electrode according to the present invention includes a response glass membrane having ion selectivity and made of oxynitride glass containing Li.

The oxynitride glass means glass in which a part of X—O bonds (where X indicates Si, B or the like) in oxide glass are substituted with X—N bonds. While O in the X—O bonds is bivalent, N in the X—N bonds is trivalent. Due to this, the number of bonds in a glass structure increases to make the glass denser and higher in mechanical strength. In addition, it is considered that the X—N bond is higher in binding force than the X—O bond.

Furthermore, while an ion radius of oxygen is about 1.40 Å, an ion radius of nitrogen is about 1.71 Å. Due to this, if the X—O bonds in the oxide glass are substituted with the X—N bonds, voids are made larger in a mesh structure of the glass.

Due to this, according to the present invention, the mechanical strength of the response glass membrane increases, a chemical strength thereof increases, resistances of the glass against water, acid, alkali, heat and the like improve, and durability of the glass improves. Further, according to the present invention, the voids are made larger in the mesh structure of the glass to make $Li^+$ easier to move in the glass. Therefore, it is possible to reduce membrane resistance and improve ion response.

It is preferable that the oxynitride glass contains at least one element selected from the group consisting of Groups 3 and 13 elements. Specifically, examples of the Group 3 elements include La and those of the Group 13 elements include Al. If the oxynitride glass contains the Group 3 element such as La, proton selectivity of the oxynitride glass improves. If the oxynitride glass contains the Group 13 element such as Al, alkali metal (Na, K or the like) selectivity thereof improves.

If a Group 2 element such as Mg, Ca, Sr or Ba is mixed in the oxynitride glass, it is possible to reduce alkali error that causes deterioration in measurement accuracy at time of measuring ion concentration and to increase the mechanical strength of the oxynitride glass by tightening the structure of the glass.

It is preferable that the oxynitride glass is silicate-based glass, borate-based glass or borosilicate-based glass.

Furthermore, it is more preferable that the oxynitride glass is silicate-based oxynitride glass which is excellent in corrosion resistance and in which a part of Si—O bonds in silicate glass are substituted with Si—N bonds. Examples of glass having proton selectivity among such silicate-based oxynitride glasses include glass containing at least $SiO_2$, $Li_2O$, and $Si_3N_4$ as raw materials.

The ion-selective electrode according to the present invention preferably further includes a sling tube made of oxynitride glass containing not only Li but also at least one element selected from the group consisting of Na, K, and Cs. If the response glass membrane and the sling tube are made of different types of glasses having different coefficients of expansion, then the response glass membrane and the sling tube expand or contract according to an increase or a decrease in temperature, and a junction between the glasses often cracks. By contrast, if the oxynitride glass is used for the sling tube similarly to the response glass membrane, it is possible to prevent such cracking from occurring.

According to the present invention, there is also provided a response glass membrane having ion selectivity and made of oxynitride glass containing Li.

Effects of the Invention

In this way, according to the present invention, it is possible to increase the chemical strength according to an increase in the mechanical strength, improve the resistances against water, acid, alkali, heat and the like to improve the durability, and also possible to reduce the membrane resistance to improve the ion response.

DESCRIPTION OF REFERENCE SYMBOLS

Figure 1:
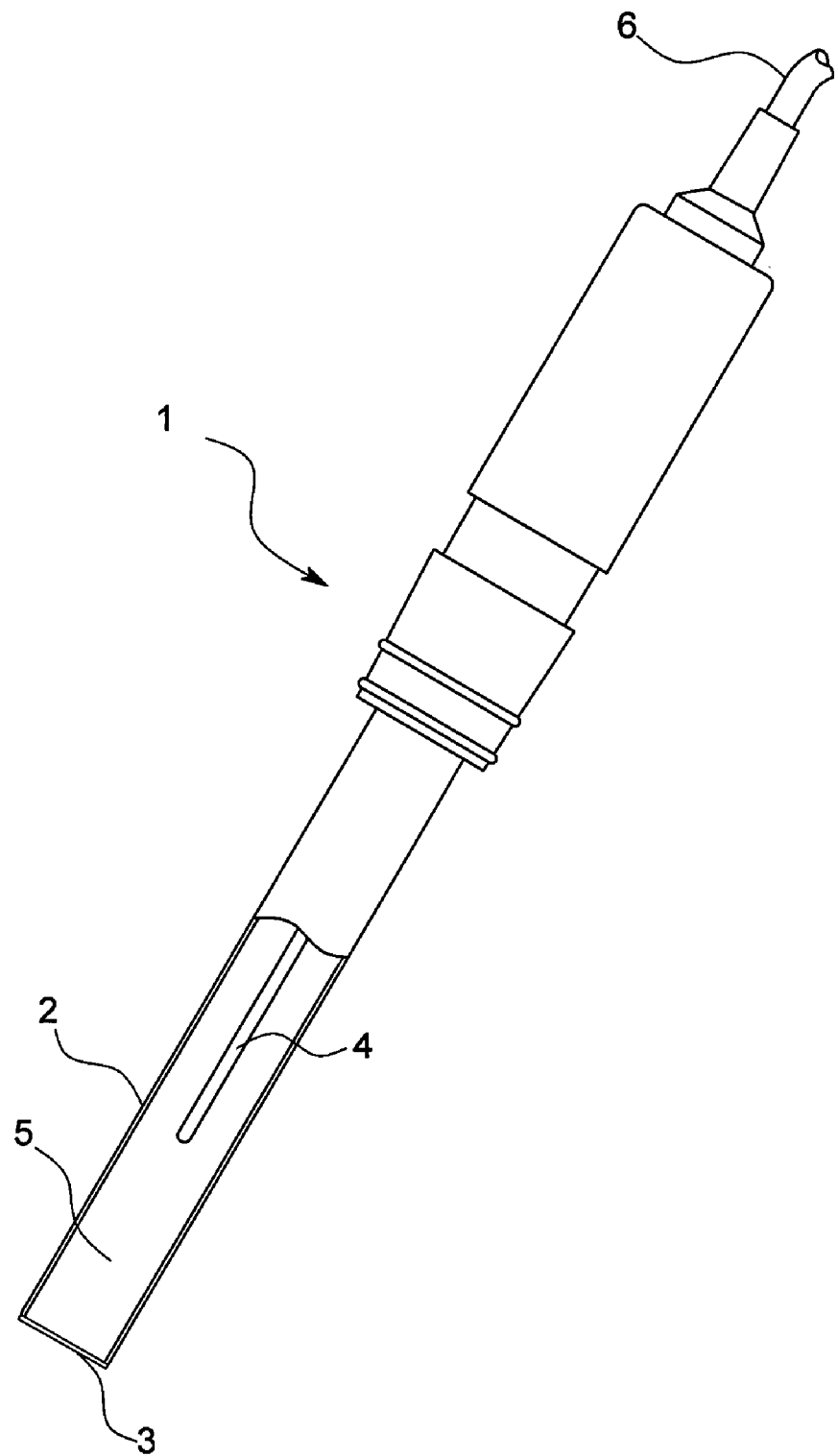
FIG. 1 is a partially cutaway showing a part of an internal structure of a pH glass electrode according to an embodiment of the present invention.
Figure 2:
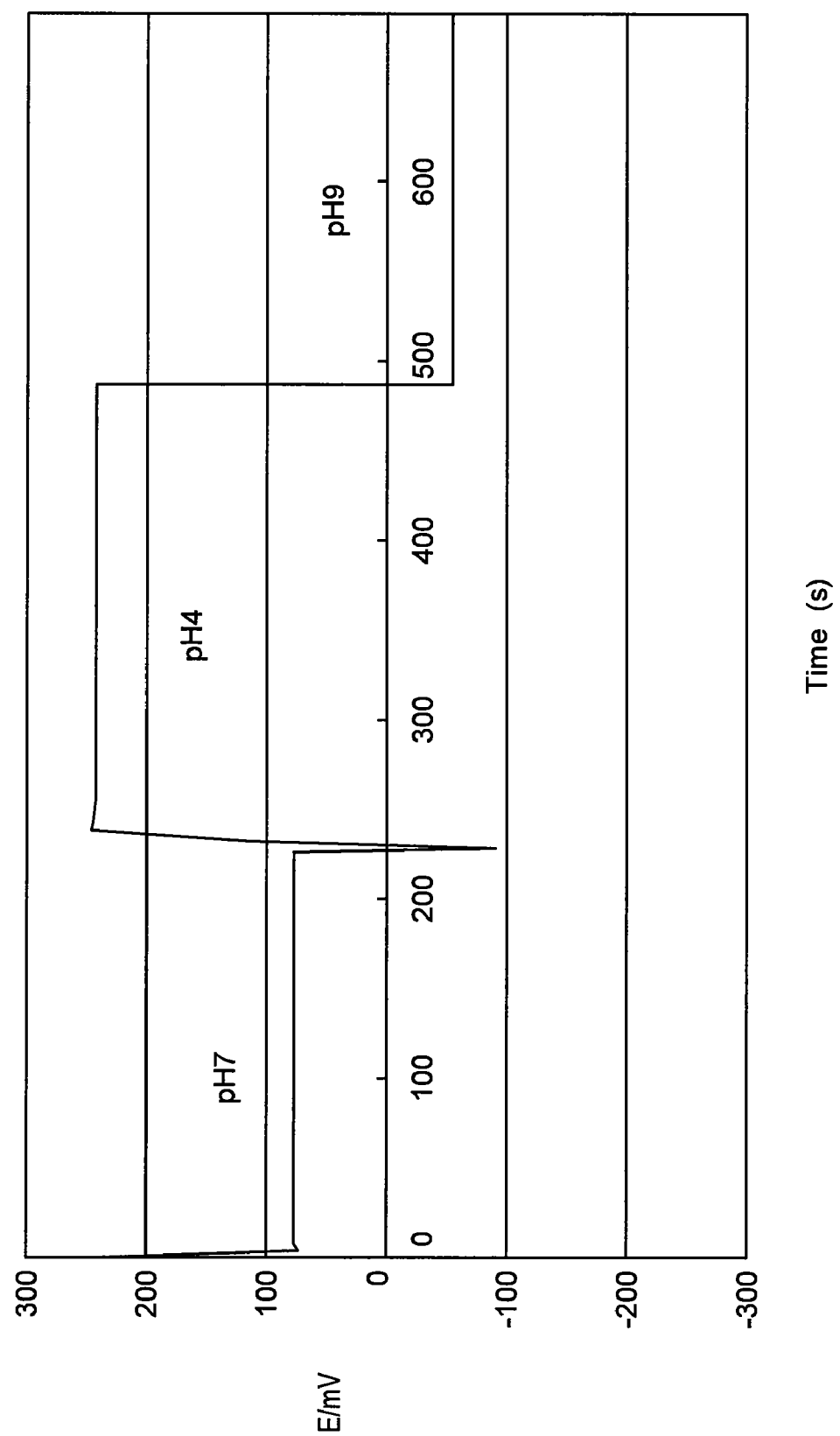
FIG. 2 is a graph showing stability of a pH measurement cell including a response glass membrane made of oxynitride glass having a composition of $30Li_2O.67SiO_2.Si_3N_4$.

1 . . . pH glass electrode
2 . . . Sling tube
3 . . . Response glass membrane
4 . . . Internal electrode
5 . . . Internal liquid
6 . . . Lead wire.

BEST MODE FOR CARRYING OUT THE INVENTION

A pH glass electrode as an ion-selective electrode according to an embodiment of the present invention will be described hereinafter referring to the drawings.

A pH glass electrode 1 according to the embodiment of the present invention includes a cylindrical glass sling tube 2 and a disc response glass membrane 3 bonded to a tip end of the sling tube 2 as shown in FIG. 1. The sling tube 2 accommodates therein an internal electrode 4 and is filled with internal liquid 5. A lead wire 6 is connected to the internal electrode 4 so as to be connected to a pH meter main body (not shown) extending to outside from a proximal end of this sling tube 2.

The response glass membrane 3 is made of oxynitride glass having ion selectivity and containing Li. Examples of the oxynitride glass include silicate-based oxynitride glass, borate-based oxynitride glass, and borosilicate-based oxynitride glass. The borosilicate-based oxynitride glass is particularly preferably used because of high corrosion resistance. It is to be noted that phosphate-based oxynitride glass cannot be used for the response glass membrane 3 since the phosphate-based oxynitride glass does not exhibit ion selectivity, is low in mechanical strength, and inferior in durability.

Examples of proton-selective glass among such borosilicate-based oxynitride glass having the ion selectivity and containing Li include glass having a material composition shown in Table 1.

TABLE 1

|  | mol % |
| --- | --- |
| SiO2 | 40-60 |
| Li2O | 20-30 |
| Si3N4 | 1-10 |
| Alkali-earth metal oxide | 1-10 |
| Rare-earth oxide | 0.1-5 |
| Network constituent substance | 1-10 |

In the Table 1, examples of the alkali-earth metal oxide include Ca, Sr, and Ba oxides. Examples of the rare-earth oxide include an La oxide. Examples of the network constituent substance include $Ta_2O_5$, $ZrO_2$, and $TiO_2$.

It is to be noted that it is possible to obtain glass having sodium or potassium selectivity by adding an Al-containing compound such as $Al_2O_3$ or AlN to components shown in the Table 1.

At time of manufacturing the oxynitride glass, if a conventional oxide glass melting method (a method including mixing powders of metal compounds serving as materials, melting powder mixture at high temperature to turn the powder mixture into a liquid state, appropriately molding the liquid, and quenching the resultant compact) is used, nitrogen possibly gasifies and volatilizes. Considering this, the response glass membrane made of silicate glass is produced first, and the response glass membrane is temporarily pulverized to powder. That is, in case of the glass shown in the Table 1, the response glass membrane made of silicate glass containing $SiO_2$, $Li_2O$, the alkali earth-metal oxide, the rare-earth oxide, and the network constituent substance as materials is produced and temporarily pulverized to powder.

Next, silicon nitride powder ($Si_3N_4$ in the Table 1) is mixed into the obtained powder, and molten at 1300° C. to 1400° C. for about one hour while pressing the powder mixture in an atmosphere of ammonium gas or nitrogen (in reducing atmosphere) and bubbling the ammonium gas or nitrogen, thereby obtaining oxynitride glass. Alternatively, the oxynitride glass can be obtained by pressing and melting silicate glass powder in the atmosphere of ammonium gas or nitrogen into the silicate glass powder without mixing the silicon nitride powder.

The response glass membrane 3 is produced by cutting and polishing the obtained oxynitride glass into a plate shape. Alternatively, the response glass membrane 3 can be produced by pouring molten oxynitride glass into a predetermined die and molding the molten oxynitride glass. If the oxynitride glass is subjected to blow molding into a generally semispherical shape similarly to the conventional response glass membrane 3, nitrogen possibly volatilizes from the oxynitride glass.

Next, the obtained response glass membrane 3 is bonded to an opening of one end of the sling tube 2 using adhesive or a mechanical mechanism (mechanical seal) and sealed, thereby producing the pH glass electrode 1. If fused junction is carried out when the sling tube 2 is bonded to the response glass membrane 3, nitrogen possibly volatilizes from the response glass membrane 3.

In case of the glass having the material composition shown in the Table 1, if a residual amount of $Si_3N_4$ at time of vitrification after melting is equal to or larger than 0.5 mol %, it is estimated that the glass expresses proton selectivity. Therefore, it is considered to be able to obtain the oxynitride glass even if the conventional oxide glass melting method is used.

The sling tube 2 bonded to the response glass membrane 3 may be made of conventional silicate glass. However, if the response glass membrane 3 and the sling tube 2 are made of different types of glasses having different coefficients of expansion, a junction where the response glass membrane 3 is bonded to the sling tube 2 often cracks because of great difference between the response glass membrane 3 and the sling tube 2 in a degree of expansion or contraction according to an increase or a decrease in temperatures of the response glass membrane 3 and the sling tube 2. It is, therefore, preferable to use the oxynitride glass for the sling tube 2 similarly to the response glass membrane 3. As the oxynitride glass used for the sling tube 2, it is preferable to use oxynitride glass containing not only Li but also an element such as Na, K or Cs.

The sling tube 2 needs insulating property equal to or higher than $10^{12}Ω$. If the oxynitride glass containing not only Li but also Na, K, Cs or the like as stated above is used for the sling tube 2, it is possible to greatly reduce electrical conductivity of the glass by mixture alkali effect and to sufficiently increase electrical resistance of the glass by substituting a part of Li with the other alkali metal element such as Na, K or Cs for the following reason. $Na^+$, $K^+$ or $Cs^+$ is larger in ion radius than $Li^+$ and moves in cavities of the mesh structure of the glass less easily than $Li^+$.

If the oxynitride glass is used for the sling tube 2 similarly to the response glass membrane 3, it is possible to integrally form the sling tube 2 and the response glass membrane 3.

As the internal electrode 4, a silver chloride electrode is used, for example. As the internal liquid 5, a potassium chloride solution having a pH prepared to 7 is used, for example.

At time of measuring a pH of a sample solution using the pH glass electrode 1, if the response glass membrane 3 of the pH glass electrode 1 is immersed in the sample solution the pH of which is to be measured, an electromotive force is generated on the response glass 3 according to a pH difference between the internal liquid 5 and the sample solution. This electromotive force is measured as a potential difference (voltage) between the internal electrode 4 of the pH glass electrode 1 and an internal electrode of a comparison electrode (not shown) using the comparison electrode, thereby calculating the pH of the sample solution. This electromotive force changes according to temperature. Due to this, it is preferable to use a temperature element to correct the potential difference using a value of a signal output from the temperature element as a parameter, to calculate the pH of the sample solution, and to display the pH on the pH meter main body.

The present invention is not limited to the above-stated embodiment.

The ion-selective electrode according to the present invention is not limited to an independent type electrode such as the pH glass electrode 1. Alternatively, the ion-selective electrode according to the present invention may be a composite electrode obtained by integrating a glass electrode with a comparison electrode or one electrode obtained by further adding a temperature compensation electrode to the composite electrode and integrating the temperature compensation electrode with the composite electrode.

Needless to say, various changes and modification can be made of the present invention within a scope without departure from the spirit of the present invention.

EXAMPLES

The present invention will be described in more detail while referring to examples below. However, the present invention is not limited to the examples.

A pH measurement cell that includes a response glass membrane (thickness of 3.2 mm) made of oxynitride glass having the composition of $30Li_2O \cdot 67SiO_2 \cdot Si_3N_4$ was produced. Potentials were measured using standard liquids having pH 4, 7, and 9 with a potential of a double junction comparison electrode (manufactured by HORIBA, Ltd., #2565) set as a reference.

Evaluation was made for two items, that is, reproducibility and response. Specifically, the reproducibility was evaluated by repeatedly measuring the potentials of the respective standard liquids twice. The response was evaluated by measuring response time (time since a measurement-target standard liquid is switched to another until a potential reaches a range from −1 mV to +1 mV with respect to a potential three minutes after the potential is considered stable). Table 2 shows a measurement result related to the reproducibility and Table 3 shows a measurement result related to the response.

TABLE 2

|  | First | Second |
|---|---|---|
| pH 7 | 78.3 | 78.1 |
| pH 4 | 240.9 | 237.4 |
| pH 9 | −56.2 | −56.9 |

In the Table 2, unit is "mV".

TABLE 3

|  | Comparison | Product according to present invention |
|---|---|---|
| Between pH 7 and pH 4 | 60 | 5 |
| Between pH 7 and pH 9 | 40 | 5 |

In the Table 3, unit is "second".

In the evaluation of the response, a pH electrode referred to as "tough electrode" including a response glass membrane thicker than an ordinary response glass membrane so as to improve durability, that is, having a thickness of 0.5 mm was used as a comparison. Although the response glass membrane of the product according to the present invention is six times thicker than the response glass membrane of the comparison, the product according to the present invention was eight times or more as high as the comparison in the response. It was found that the product according to the present invention was innovative in that both the durability and the response that were conventionally considered to be contradictory properties against each other improved.

INDUSTRIAL APPLICABILITY

The present invention can provide an ion-selective electrode excellent in both durability and response that are conventionally considered to be contradictory properties.

The invention claimed is:

1. An ion-selective electrode comprising:
   a response glass membrane having ion selectivity and made of oxynitride glass in which a part of O in an oxide glass are substituted with N containing Li.

2. The ion-selective electrode according to claim 1, wherein
   the oxynitride glass contains at least one element selected from the group consisting of Groups 3 and 13 elements.

3. The ion-selective electrode according to claim 1, wherein
   the oxynitride glass is silicate-based oxynitride glass, borate-based oxynitride glass or borosilicate-based oxynitride glass.

4. The ion-selective electrode according to claim 3, wherein
   the silicate-based oxynitride glass contains at least $SiO_2$, $Li_2O$, and $Si_3N_4$ as raw materials.

5. An ion-selective electrode comprising:
   a sling tube made of oxynitride glass containing not only Li but also at least one element selected from the group consisting of Na, K, and Cs and having an insulating property equal to or higher than $10^{12}\Omega$; and
   a response glass membrane having ion selectivity and made of oxynitride glass in which a part of O in an oxide glass are substituted with N containing Li.

6. The ion-selective electrode according to claim 5, wherein
the oxynitride glass contains at least one element selected from the group consisting of Groups 3 and 13 elements.

7. The ion-selective electrode according to claim 5, wherein
the oxynitride glass is silicate-based oxynitride glass, borate-based oxynitride glass or borosilicate-based oxynitride glass.

8. The ion-selective electrode according to claim 7, wherein
the silicate-based oxynitride glass contains at least $SiO_2$, $Li_2O$, and $Si_3N_4$ as raw materials.

9. An ion-selective electrode comprising:
a sling tube made of oxynitride glass containing not only Li but also at least one element elected from the group consisting of Na, K, and Cs; and
a response glass membrane having ion selectivity and made of oxynitride glass in which a part of O in an oxide glass are substituted with N containing Li.

10. The ion-selective electrode according to claim 9, wherein
the oxynitride glass contains at least one element selected from the group consisting of Groups 3 and 13 elements.

11. The ion-selective electrode according to claim 9, wherein
the oxynitride glass is silicate-based oxynitride glass, borate-based oxynitride glass or borosilicate-based oxynitride glass.

12. The ion-selective electrode according to claim 11, wherein
the silicate-based oxynitride glass contains at least $SiO_2$, $Li_2O$, and $Si_3N_4$ as raw materials.

* * * * *